(12) United States Patent
Agnihorti et al.

(10) Patent No.: US 8,185,511 B2
(45) Date of Patent: May 22, 2012

(54) CLINICIAN-DRIVEN EXAMPLE-BASED COMPUTER-AIDED DIAGNOSIS

(75) Inventors: Lalitha Agnihorti, Tarrytown, NY (US);
Lilla Boroczky, Mount Kisco, NY (US);
Luyin Zhao, Belleville, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 355 days.

(21) Appl. No.: 12/305,089

(22) PCT Filed: Jun. 15, 2007

(86) PCT No.: PCT/IB2007/052307
§ 371 (c)(1),
(2), (4) Date: Dec. 16, 2008

(87) PCT Pub. No.: WO2007/144854
PCT Pub. Date: Dec. 21, 2007

(65) Prior Publication Data
US 2009/0138432 A1    May 28, 2009

Related U.S. Application Data

(60) Provisional application No. 60/804,955, filed on Jun. 16, 2006.

(51) Int. Cl.
*G06F 17/30* (2006.01)
(52) U.S. Cl. ...................................... 707/706
(58) Field of Classification Search ........... 707/2, 104.1, 707/706; 382/131
See application file for complete search history.

(56) References Cited

U.S. PATENT DOCUMENTS
2003/0103663 A1* 6/2003 Li et al. .......................... 382/131

FOREIGN PATENT DOCUMENTS
WO           0157777 A2      8/2001
WO     2005073916 A1      8/2005

OTHER PUBLICATIONS

Celebi M. E. et al., "Content-based image retrieval incorporating models of human perception", Information Technology: Coding and Computing, 2004, pp. 241-245, vol. 2, Piscataway, NJ, US.
Li Qiang et al, "Investigation of new psychophysical measures for evaluation of similar images on thoracic computed tomography for distinction between benign and malignant nodules", Medical Physics, 2003, pp. 2584-2593, vol. 30, No. 10, Melville, NY, US.
Liyang Wei et al, "Learning of perceptual similarity from expert readers for mammogram retrieval", Biomedical Imaging: Macro to Nano, 2006, pp. 1356-1359, Piscataway, NJ, US.

(Continued)

Primary Examiner — Etienne LeRoux (57) ABSTRACT

Optimizing example-based computer-aided diagnosis (CADx) is accomplished by clustering volumes-of-interest (VOIs) (116) in a database (120) into respective clusters according to subjective assessment of similarity (S220). An optimal set of volume-of-interest (VOI) features is then selected for fetching examples such that objective assessment of similarity, based on the selected features, clusters, in a feature space, the database VOIs so as to conform to the subjectively-based clustering (S230). The fetched examples are displayed alongside the VOI to be diagnosed for comparison by the clinician. Preferably, the displayed example is user-selectable for further display of prognosis, therapy information, follow up information, current status, and/or clinical information retrieved from an electronic medical record (S260).

22 Claims, 4 Drawing Sheets

OTHER PUBLICATIONS

Bo Yuan et al, "Evolutionary fuzzy c-means clustering algorithm", Fuzzy Systems, 1995, pp. 2221-2226, vol. 4.

Syng-Yup Ohn et al, "Determining optimal decision model for support vector machine by genetic algorithm", Computational and Information Science, 2004, pp. 895-902, vol. 3314, Berlin, DE.

Boroczky L et al, "Feature subset selection for improving the performance of false positive reduction in lung nodule CAD", Computer-based Medical Systems, 2005, pp. 85-90, Piscataway, NJ, US.

Naqa, Issam El et al, "Content-Based image retrieval for digital mammography", Int. Conf. Image Processing, Jun. 2002, pp. 141-144, vol. 3.

Lofty H.M. et al, "A novel cluster-based image retrieval", Symposium on Signal Processing and Information Technology, Dec. 2004, pp. 338-341.

Bezdek, J.C.,"Pattern Recognition with Fuzzy Objective Function Algorithms",1981, pp. 65-86, Plenum Press, New York.

* cited by examiner

| | 1 | 2 | 3 | 4 | • | • | • | 10 |
|---|---|---|---|---|---|---|---|---|
| 1 | S | 2 | | 1 | | | | 1 |
| 2 | S | S | | S | | | | 3 |
| 3 | D | 1 | | D | 2 | | | 2 |
| 4 | | | | S | | | | |

| VOI | 1 | 2 | 3 | 4 | • | • | • | 98 | 99 | 100 |
|---|---|---|---|---|---|---|---|---|---|---|
| 1 | S | D | S | S | ? | | | | S | S |
| 2 | D | S | ? | ? | S | ? | | S | D | D |
| 3 | S | ? | S | S | | S | ? | | D | D |
| 4 | S | ? | S | S | | S | D | | ? | ? |
| • | ? | S | D | D | | | | | ? | S |
| • | | | | | | | | | S | ? |

FIG. 4

CLINICIAN-DRIVEN EXAMPLE-BASED COMPUTER-AIDED DIAGNOSIS

The present invention relates to example-based computer-aided diagnosis and, more particularly, to selecting an optimal set of volume-of-interest (VOI) features by which to fetch examples from a database.

Radiologists have to read many images of scans produced by computed tomography (CT), X-rays, magnetic resonance imaging (MRI), ultrasound, positron emission tomography (PET), etc. This may lead to "information overload" for the radiologists. Furthermore, radiologists may miss many cancers during interpretation of images in cancer screenings, for example. Information overload potentially aggravates this problem. Even if a subsequent scan detects the cancer, survival rate can be increased by early diagnosis. Conversely, false positives can result in unnecessary biopsies. Decision support systems such as computer-aided diagnosis (CADx) schemes are, as a consequence, increasingly being utilized, to improve both workflow and patient outcomes.

The background of the example based CADx system is that clinicians acquire knowledge by experience and referring to cases that they have seen before. One way, in which a decision support system can assist a clinician in making a diagnosis of a CT scan (or any other modality scans X-rays, magnetic resonance imaging (MRI), ultrasound, positron emission tomography (PET), etc.) of for example, lung cancer, is to offer previous images that have been diagnosed and are similar to the new one. An example-based paradigm is that nodules similar to the one to be diagnosed are retrieved from a database of nodules with known diagnosis and presented to the radiologist. This is the basic premise of an example-based CADx system.

Example-based or case-based CADx typically involves fetching, from a database, information particular to tumors or lesions of known pathology, i.e., malignant or benign. The information typically includes an image of the tumor for visual comparison with an image of the tumor to be diagnosed. The tumor may be in the patient's lung, for example. Image data of the tumor may be captured by any one of a number of imaging techniques, some of which are mentioned above. From the image, features of a tumor may then be measured, each feature representing a particular visual characteristic of the tumor. The tumor to be diagnosed, and the tumors of the database, can be placed in a common feature space, i.e., an N-dimensional space for which each dimension represents a respective one of N measured features. Similarity of any database tumor to the tumor to be diagnosed can tentatively and objectively be assessed based on proximity of the two tumors in the feature space. Typically, the tumors of closest proximity are fetched. The fetched examples may be displayed alongside the tumor to be diagnosed, for visual comparison. Example-based CADx can also be useful in training medical personnel in the diagnosis of scans.

The example-based CADx technique exists against a background in which clinicians acquire knowledge by experience and referring to cases that they have seen before. The present inventors have observed that different radiologists may have differing opinions on whether and how two cases are similar, and, based on a visual comparison between the tumor to be diagnosed and an image of a tumor of known pathology, it is hard to know beforehand whether or not the two cases are similar.

It is proposed herein to use the knowledge of clinicians, e.g. the radiologist, in determining a feature space, and a point-to-point distance metric to be used in gauging similarity between a tumor to be diagnosed and tumors in the database. Here, "point-to-point" includes the case of point-to-multipoint. Although, as mentioned above, knowing beforehand whether two cases are similar is difficult, judging whether a particular feature space and distance metric accord with subjective assessments of tumor similarity can be reliably evaluated according to the proposal herein. These conditions motivate the use of a genetic algorithm (GA). The GA iteratively evolves set of candidate proposed solutions to a given problem. All candidate solutions, called chromosomes, are evaluated according to their respective fitness. If an iteration stopping criterion is not met, one or more new chromosomes are reproduced based on the current set of chromosomes. Fitness is assessed and the stopping criterion is applied in the next iteration. Once the stopping criterion is met, the fittest chromosome is chosen. The instant proposal takes into account subjective assessment of similarity by radiologists in making the iteratively applied evaluation.

In brief, optimizing example-based CADx is accomplished by clustering volumes-of-interest (VOIs) in a database into respective clusters according to subjective assessment of similarity. An optimal set of volume-of-interest (VOI) features that includes image based and clinical (non-image based) features is then selected for fetching examples such that objective assessment of similarity, based on the selected features, clusters, in a feature space, the database VOIs so as to conform to the subjectively-based clustering.

Details of the novel example-based CADx technique are set forth below with the aid of the following drawings.

Figure 1:
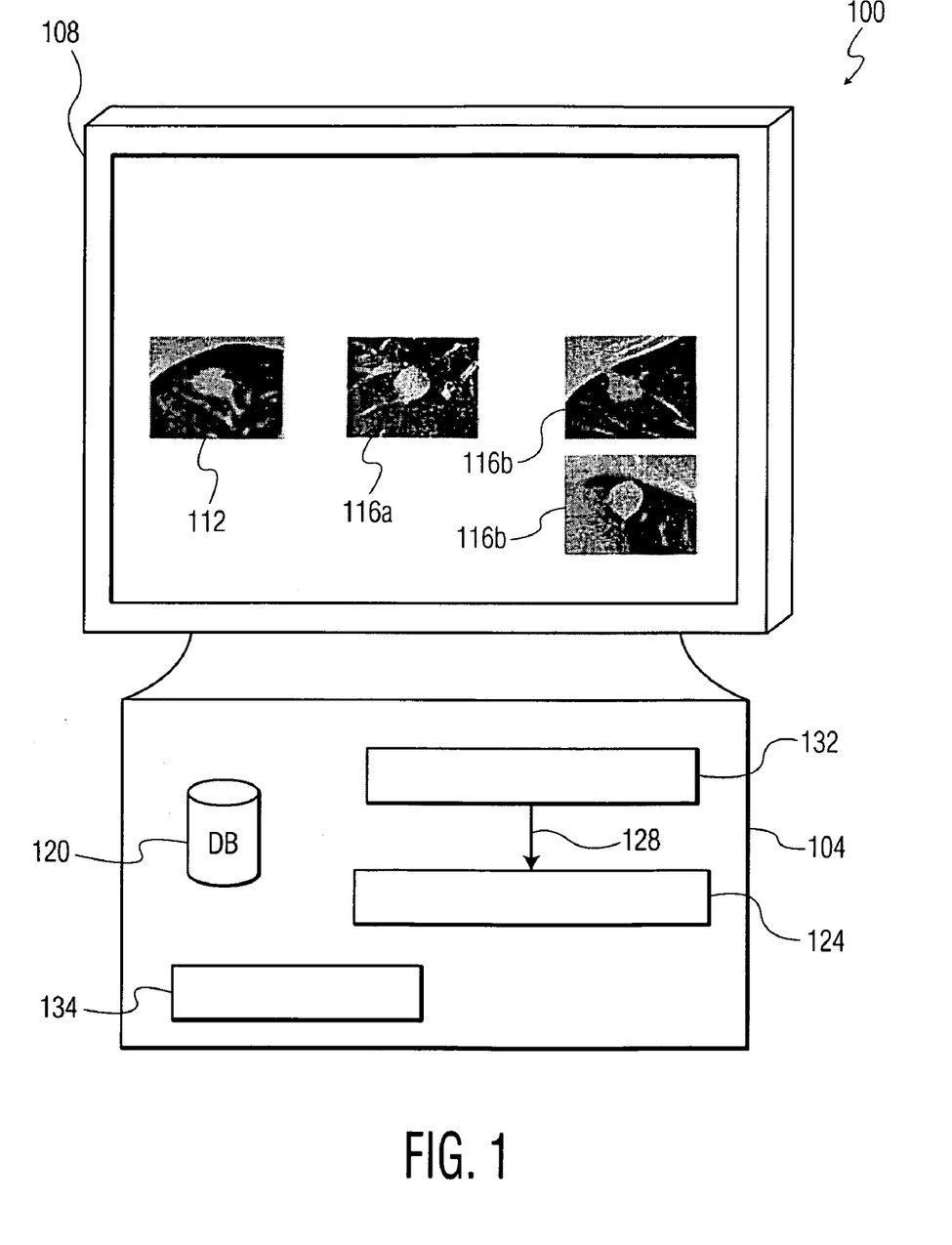
FIG. 1 is a functional diagram providing an overview of an exemplary CADx system in accordance with the present invention.

FIG. 1 depicts an example of an example-based computer aided diagnosis (CADx) device 100 according to the present invention, including a processor 104 and a display screen 108. Shown in the display screen 108 is the nodule, tumor or lesion to be diagnosed 112. Display is preferably made of some of the immediately surrounding tissue. The nodule to be displayed, and optionally some of its immediately surrounding tissue, is referred to hereinafter as a volume-of-interest (VOI). Three fetched examples are also on display alongside the VOI 112. The three examples are of a VOI 116a having a malignant tumor and two VOIs 116b having respective benign tumors. The three example VOIs 116 have been fetched from a database 120 of the processor 104, by an example-fetching module 124. The example-fetching module 124 operates based on parameters, such as image features and a similarity metric, supplied by a parameter output module (not shown), those parameters having been derived by a parameter deriving unit 132. The parameter output module is, in the shown implementation, integral with the parameter deriving unit 132. The arrow 128 represents transmission of the derived parameters for use by the example-fetching module 124. User input means 134 are used to provide the parameter deriving unit 132 with data on subjective assessment of similarity between VOIs 116. The user input means 134 might include a keyboard, mouse, trackball, slider, light pen, touch screen, etc., as well as diskette, optical disc drives and wired or wireless connections to online networks. Likewise the database 120 serves as input for the parameter deriving unit. Examples fetched by the example-fetching module 124 and displayed on-screen may selectively be chosen, as by clicking on the mouse, for display of further clinical or other information relating to the chosen example. The CADx device 100 includes a memory (not shown) for storing image data, and perhaps clinical data, of the VOI 112, which includes working memory for use by the example-fetching module 124 and the parameter deriving unit 132. The CADx device 100 may be a dedicated or general-purpose processor, and may be analog or digital. Although merely three example VOIs 116 are shown on simultaneous display, more or less may be on display, and in any practical spatial arrangement around the screen 108. Also, although the concurrent display has both types of cases, malignant and benign, merely one of the two types of cases may be on display alongside the VOI 112 at any one time. In either event, the designations "Malignant" and/or "Benign" may initially annotate the displayed examples 116, or could be brought up in response to the user's indication. In addition, the functionality may be apportioned among a different number of elements 124, 132, and distributed differently than shown. For example, the unit 132 may be located remotely from the rest of the device 100.

Figure 2:
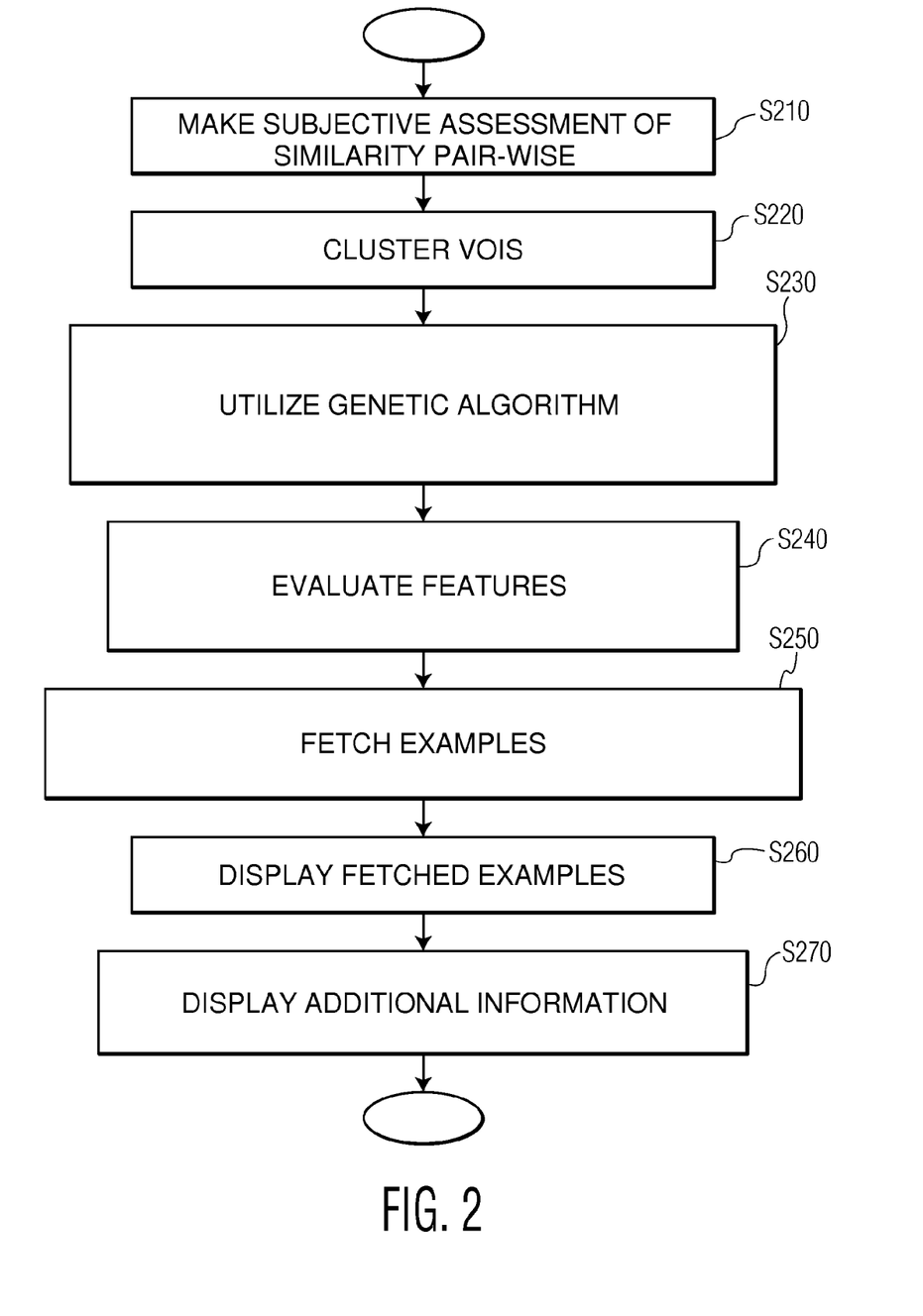
FIG. 2 is a flow chart providing an overview of one example of the methodology according to the present invention.

FIG. 2 shows, by illustrative and non-limitative example, a process 200 for example-based CADx according to the present invention. First, subjective assessment of similarity is made pair-wise over all VOIs 116 in the database 120 (step S210). The assessments are preferably made by clinicians, such as radiologists, e.g., through interviews. The assessments preferably include, in addition, subjective rankings of features according to their importance in the assessing of similarity. For the present purposes, the features of the VOI 112, 116 include extractable characteristics derivable from an image of the VOI, such as effective diameter, degree of circularity, contrast, mean gray value, angularity, margin, density, speculation, pixel standard deviation, radial gradient index, etc. Clinical data particular to the patient and the VOI, such as age, cancer history, etc., may also constitute a feature. From the assessments, similar VOIs 116 are clustered together, in the logical sense (step S220). Thus, subsets of the VOIs 116 are formed. These need not be mutually exclusive subsets. The subjectively-based clustering may be performed manually, or preferably automatically by the parameter deriving unit 132.

A genetic algorithm (GA) is utilized to find an optimal feature space, and, preferably, an optimal point-to-point similarity criterion for use in the optimal feature space (S230). The optimal feature space is to be derived from a pool of features whose member features may be derived from the subjective ranking of features in step S220. The pool of features may more inclusively contain any extractable image features, or relevant clinical data, pertaining to the VOIs 116 in the database. Candidate similarity criteria may differ from one another only with respect to the point-to-point distance metric utilized.

Each time a new chromosome is created by reproduction in the GA, fitness of the chromosome is evaluated. Since each chromosome represents a respective set of features and preferably a respective distance metric, and since the fittest chromosome is chosen at the time the stopping criterion is satisfied, each evaluation of chromosome fitness can be considered an iteration of an iterative process. Iteratively, then, a set of features and, preferably, a distance metric is chosen. Due to the nature of the fitness evaluation being proposed, the iterations tend to cause, over time, objectively-based clustering of the VOIs 116 to resemble the subjectively-based clustering of step S220. The criterion used in the fitness evaluation is the degree of similarity between the subjectively-based clustering and an objectively-based clustering which is a spatial point clustering in the feature space defined by the set of features contained in the current chromosome whose fitness is being evaluated. Preferably, the chromosome also contains a respective distance metric, which is preferably used in the objectively-based clustering.

One example of an algorithm used for the objectively-based spatial-point clustering is Fuzzy c-means (FCM). This is the preferred similarity criterion. It is a method of clustering which allows one piece of data to belong to two or more clusters. This method is frequently used in pattern recognition. It is based on minimization of the following objective function:

$$J_m = \sum_{i=1}^{N} \sum_{j=1}^{C} u_{ij}^m \|x_i - c_j\|^2, \quad 1 \le m < \infty$$

where m is any real number greater than 1, $u_{ij}$ is the degree of membership of $x_i$ in the cluster j, $x_i$ is the ith of d-dimensional measured data, $c_j$ is the d-dimension center of the cluster, $\|*\|$ is any norm expressing the similarity between any measured data and the center. To initialize the number of centers C, we can use the number of clusters formed by the subjectively-based clustering. The centers $c_j$ are initially set to correspond to the centroids of each of the objectively-based clusters in the current feature space, i.e., the feature space defined by the chromosome currently being fitness evaluated. The norm utilized is the distance metric contained in the current chromosome.

In case the metric is the Mahalanobis distance, the normed quantity in the above equation is, instead, the Mahalanobis distance between $x_i$ and the rest members of the cluster j. Likewise, in example retrieval, a group of examples with least Mahalanobis distance to the VOI 112 is retrieved. A genetic algorithm for such retrieval is provided in International Application No. WO2005073916, filed on Jan. 21, 2005 and commonly assigned with the instant patent application.

Fuzzy partitioning is carried out through an iterative optimization of the objective function shown above, with the update of membership $u_{ij}$ and the cluster centers $c_j$ by:

$$u_{ij} = \frac{1}{\sum_{k=1}^{C} \left( \frac{\|x_i - c_j\|}{\|x_i - c_k\|} \right)^{\frac{2}{m-1}}}, \quad c_j = \frac{\sum_{i=1}^{N} u_{ij}^m \cdot x_i}{\sum_{i=1}^{N} u_{ij}^m}$$

This iteration will stop when $\max_{ij}\{|u_{ij}^{(k+1)} - u_{ij}^{(k)}|\} < \epsilon$, where $\epsilon$ is a termination criterion between 0 and 1, whereas k are the iteration steps. This procedure converges to a local minimum or a saddle point of $J_m$.

The algorithm is composed of the following steps:

1. Initialize $U = [u_{ij}]$ matrix, $U^{(0)}$
2. At k-step: calculate the centers vectors $C^{(k)} = [c_j]$ with $U^{(k)}$ $$c_j = \frac{\sum_{i=1}^{N} u_{ij}^m \cdot x_i}{\sum_{i=1}^{N} u_{ij}^m}$$

3. Update $U^{(k)}$, $U^{(k+1)}$ $$u_{ij} = \frac{1}{\sum_{k=1}^{c} \left(\frac{\|x_i - c_j\|}{\|x_i - c_k\|}\right)^{\frac{2}{m-1}}}$$

4. If $\|U^{(k+1)} - U^{(k)}\| < \epsilon$ then STOP; otherwise return to step 2.

The factors in the matrix U are numbers between 0 and 1, these factors being taken from the membership function. If the coefficients in the matrix U are all 0 or 1, each datum can belong to only one cluster. This is the case (a) shown below. In case (b) membership is fuzzy.

$$U_{N \times C} = \begin{bmatrix} 1 & 0 \\ 0 & 1 \\ 1 & 0 \\ \cdots & \cdots \\ 0 & 1 \end{bmatrix} \quad (a)$$

$$U_{N \times C} = \begin{bmatrix} 0.8 & 0.2 \\ 0.3 & 0.7 \\ 0.6 & 0.4 \\ \cdots & \cdots \\ 0.9 & 0.1 \end{bmatrix} \quad (b)$$

The number of rows and columns depends on how many data and clusters we are considering. More exactly we have C=2 columns (C=2 clusters) and N rows, where C is the total number of clusters and N is the total number of data. The generic element is so indicated: $u_{ij}$.

Other properties are shown below:

$$u_{ij} \in [0, 1] \quad \forall i, j$$

$$\sum_{j=1}^{C} u_{ij} = 1 \quad \forall i$$

$$0 < \sum_{i=1}^{N} u_{ij} < N \quad \forall N$$

Further details on FCM are set forth in J. C. Dunn (1973): "A Fuzzy Relative of the ISODATA Process and Its Use in Detecting Compact Well-Separated Clusters", *Journal of Cybernetics* 3: 32-57 and the FCM technique is developed further in J. C. Bezdek (1981): "Pattern Recognition with Fuzzy Objective Function Algorithms", Plenum Press, New York, both of which are both incorporated herein by reference in their entirety.

The fitness function in the inventive example-based CADx attributes greater fitness to fewer subset membership mismatches between the objectively-based and subjectively-based clustering.

The stopping criterion of the GA may be a given number of reproduction/evaluation cycles or sufficiently high fitness of a chromosome. At the time of stopping, the fittest chromosome is chosen, thereby also choosing the corresponding set of features contained within the chromosome and, optionally, a distance metric contained within the chromosome.

The finally-chosen set of features, and optionally the finally-chosen distance metric, collectively constitutes the parameters outputted by the parameter deriving unit 132 for use by the example-fetching module 124. This finally-chosen set includes the features of the VOI 112 to be evaluated in placing the VOI 112 in feature space (step S240). The feature space is the one finally chosen, i.e., the feature space defined by the finally-chosen set of features. Preferably all of the VOIs 116 are also evaluated so as to be correspondingly located in the feature space.

In a preferred embodiment which includes the distance metric in the GA chromosome, the finally chosen distance metric is preferably utilized by the optimal point-to-point similarity criterion, and by the example-fetching module 124 in retrieving examples 116 from the database 120 for display on-screen (step S250). Thus, examples of minimum distance from the VOI 112 are retrieved. Among the distance metrics usable are Euclidean distance, city block distance, and Mahalanobis distance. Preferably, the fetched examples are displayed alongside the VOI 112 to be diagnosed for visual comparison by the clinician (step S260). Next to each example 116 is preferably displayed an indication of how similar the example is to the VOI 112. The displayed similarity figure is based on the distance from the VOI 112. Closer examples 116 are deemed to be more similar, and examples further away are deemed to be less similar. The distance can be compared to a reference distance to produce a metric for on-screen display, such as a percentage. One example 116 might be 90% similar, while another is merely 80% similar. A cutoff might be set automatically, based on hospital protocol for instance, or set according to user discretion, so that similarity less than the cutoff suppresses display of that example 116.

In a preferred embodiment, the on-screen examples are individually selectable by the user, as by using the mouse, for further information. For each of the examples 116 in the database 120, a clinician has made a diagnosis, which is preferably backed by a determination of ground truth relating to pathology. The ground truth of pathology is elicited by means of a biopsy, other surgical procedure, or observation of the course of the disease, for example. A prognosis may also have been made for the patient. Moreover, an electronic medical record (EMR) maintained at the institution makes available the medical history, which will normally indicate types of treatment administered, such as chemotherapy or surgery, and the ensuing outcome or outcomes. Ready access to particular patient data would also be desirable. Chemotherapy may, for example, not have led to a successful outcome in an elderly patient; whereas, the same treatment for a similar tumor might be suitable for a younger patient. One course of therapy may have led to a longer patient lifetime, but at a relatively diminished quality of life. Accordingly, information on prognosis, therapy planning, and other pertinent patient data, obtainable through the EMR or otherwise, are preferably immediately available to the user by selecting menus, hyperlinks, etc. accompanying the displayed example 116 (step S270). In particular, then, the displayed example is preferably user-selectable for further display of prognosis, therapy information, follow up information, current status, and/or clinical information retrieved from the EMR. If the more than one scan for the same patient results in multiple VOIs 116 in the database 120, the linked information that can be called up on-screen may have multiple links, each to a respective example.

Figure 3:
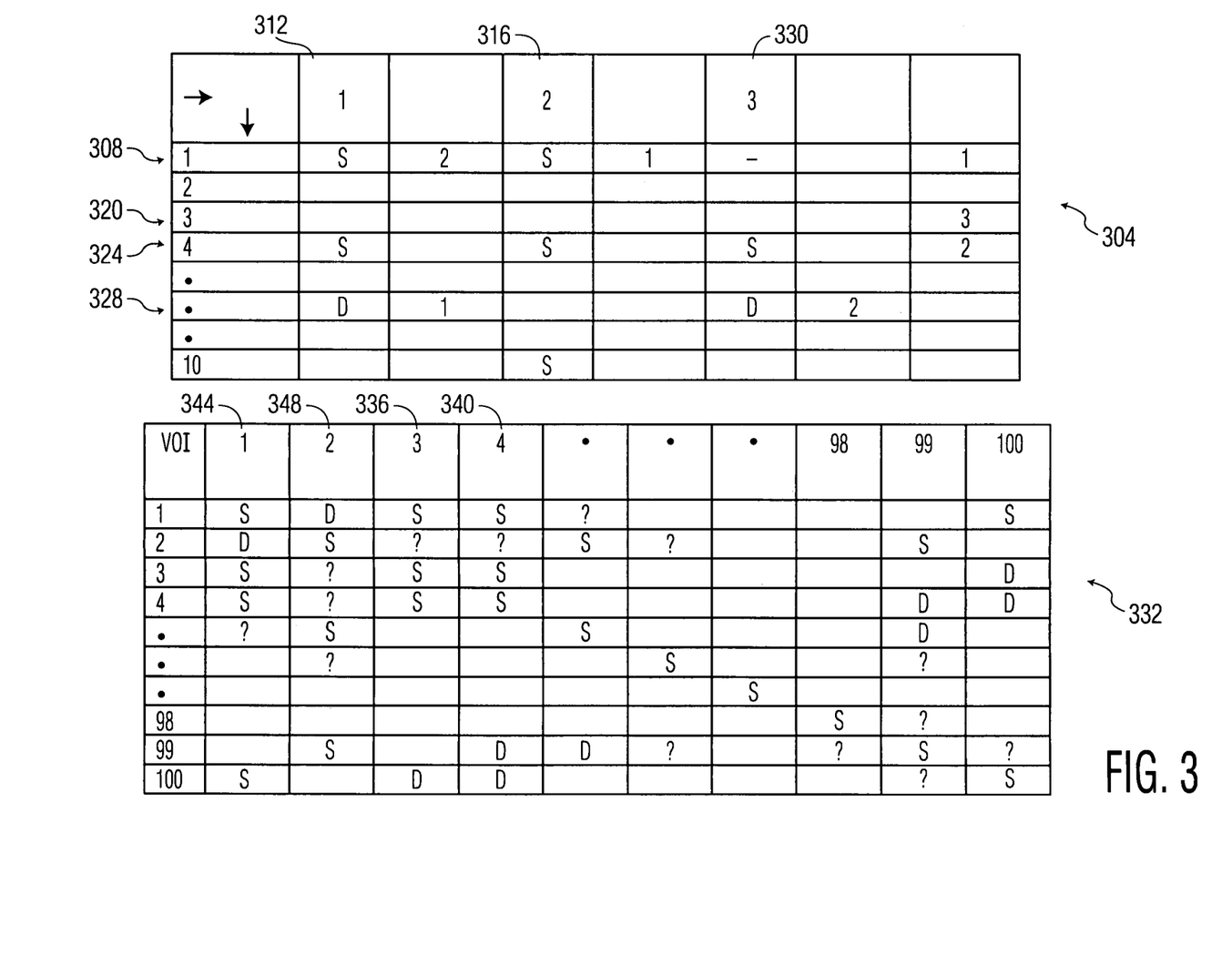
FIG. 3 illustrates tables that may be used in subjectively assessing similarity between tumors in the database so as to form clusters of similar tumors, in accordance with the present invention.

FIG. 3 provides tables that can be used in subjectively assessing similarity among the VOIs 116. As an example, a clinician being interviewed can be presented with 11 of the VOIs 116. One of the 11 serves as a reference, and the other ten are compared to the reference.

The VOI comparison and feature ranking table 304 has one row for each of the ten VOIs.

The first 308 of the ten VOIs is judged by a clinician to be similar to the reference, by virtue of a first feature 312. An "S" is therefore inserted in the (1, 1) entry. Similarity is generally assessed visually from images of the VOIs 116, although some features may be items of clinical data as mentioned above. Likewise, the clinician assesses similarity based on a second feature 316, and a corresponding "S" entry is inserted in the (1, 3) entry. The clinician designates the second feature 316 as being more important in assessing similarity of the two VOIs than the first feature 312, and accordingly ranks the second feature higher with a one. Overall among the ten VOIs, this first VOI 308 in row 1 is designated most similar to the reference, with a rank of one. As seen from row 2, the clinician reached no conclusion on similarity. A third VOI 320 was assessed similar to the reference, but the clinician provided no information on which features led to the assessment, or to an overall rank in similarity. For a fourth VOI 324, three features are indicated, but they are not ranked as to their relative importance in reaching an overall rank in similarity. The same raw data may be supplied as to dissimilarity. Thus, an eighth VOI 328 is judged be dissimilar to the reference, where the first feature 312 is of greater importance in that assessment than a third feature 330. The process of comparing ten VOIs 116 to a reference is repeated with different VOIs/references for each table 304.

Preferably, different clinicians make the assessments. The intent is to achieve a "ground truth of similarity/dissimilarity." Sometimes, the clinician can point out the features that lead to his or her conclusion. However, the clinician may reach the conclusion without knowing specifically why. Ground truth inherent in this latter case is also captured as a component of the overall ground truth represented by the consequent subjective-based clustering. In a preferred embodiment, no disclosure is made to the clinicians of the pathological status, i.e., malignant or benign, of the VOI 116 or the reference. This is to prevent biasing the clinician's judgment of similarity. However, it is alternatively possible to disclose pathology beforehand.

To minimize the number of comparisons required at this raw-data collection stage, it may be assumed that two VOIs 116 are similar if they are both similar to the same reference. When a sufficient amount of information on similarity/dissimilarity has been collected, final assessments are made on pair-wise similarity, and then on clustering.

The final assessments on pair-wise similarity are entered in a similarity/dissimilarity table 332. The table is a symmetric matrix, whose diagonal entries all indicate similarity with an "S" entry. Since VOIs 336, 340 in the third and fourth rows (columns) are similar to VOI 344 in the first row (column), they are similar to each other, as indicated by the "S" in the (3, 4) and (4, 3) entries. A VOI 348 in the second row (column) is dissimilar to the VOI 344, as shown by the entry "D" in the matrix position (1, 2) or (2, 1). Accordingly, VOIs 336, 340, 344 in the first, third and fourth rows are in the same cluster, and the VOI 348 in the second row is not in that cluster. A question mark (?) in a table entry indicates that the corresponding VOIs are both assessed to be dissimilar to a common reference, and that no further assessments exist that indicate similarity or dissimilarity between the two VOIs. Careful selection of VOIs 116 for assessment at the VOI comparison and feature ranking table 304 stage should minimize the number of question-marked entries. The question-marked entries can also be replaced based on further input from the radiologists. In the event that two different VOI comparison and feature ranking tables 304 conflict in the respective assessments of similarity/dissimilarity between a particular pair of VOIs 116, the presence or non-presence of feature ranking, and the overall rank if available, may be used to resolve the conflict one way or the other.

Figure 4:
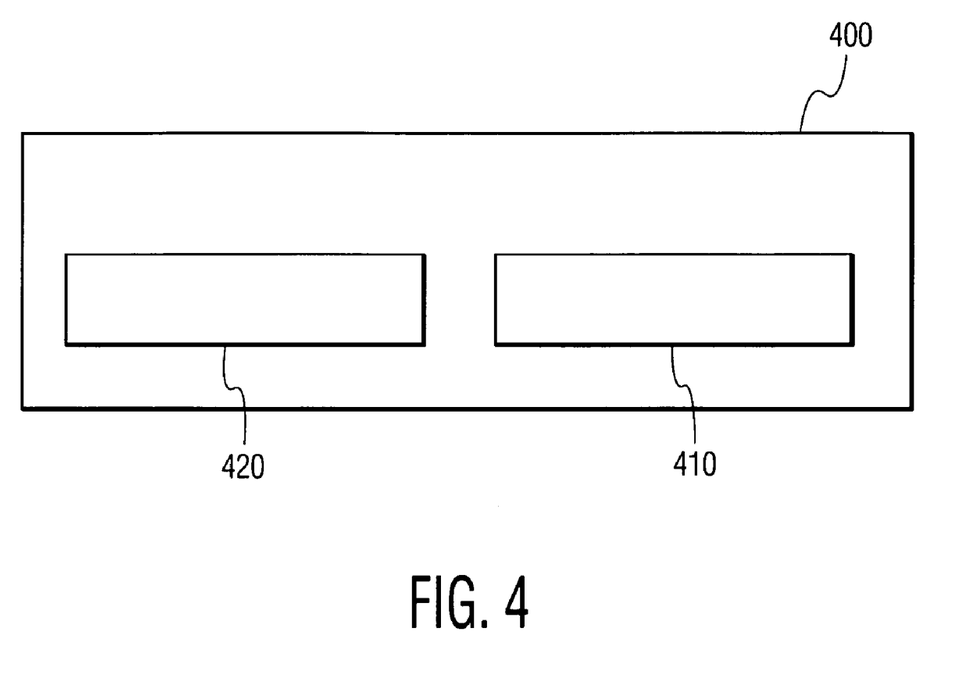
FIG. 4 is a block diagram of a chromosome usable in a genetic algorithm according to the present invention.

FIG. 4 portrays an exemplary format of a current chromosome 400 to be subject to fitness evaluation in the GA. The chromosome 400 includes a feature bit map 410 and a distance metric index 420. The feature bit map 410 is comprised of one bit for each feature in the feature pool. If the bit is set, i.e., one rather than zero, the feature corresponding to the set bit is one of the features in the set of features that is contained in the chromosome 400. Thus, if 10 bits are set, this chromosome represents a 10-dimensional feature space whose dimensions are each of the features indicated by a respective set bit. The distance metric index 420 has a length of ceiling ($\log_2(M)$) bits, where M is the number of candidate distance metrics, and the ceiling function returns the smallest integer greater than its argument. Accordingly, if M=10, the distance metric index is 4 bits long.

The GA rules preferably entail, as a combination technique, swapping of trailing bits of the index 420 and trailing bits of the map 410. The cutoff bit can fixed or made to vary randomly. Mutation, as another reproductive technique, can be invoked relatively sparsely in the temporal sense. To achieve faster convergence to optimality, feature rankings in the VOI comparison and feature ranking table 304 be used in setting feature bits in the initial population of chromosomes.

While there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, a user interface may allow designation of feature weights for respective distance metrics. It should be recognized that structures and/or elements and/or method steps shown and/or described in connection with any disclosed form or embodiment of the invention may be incorporated in any other disclosed or described or suggested form or embodiment as a general matter of design choice.

The invention claimed is:

1. A device that optimizes example-based computer-aided diagnosis of a patient based on a medical image of the patient, comprising:

a parameter deriving unit configured to select an optimal set of volume-of-interest (VOI) features by which to fetch examples such that an objective assessment of similarity clustering of volumes-of-interest (VOIs) occurs in a database so as to conform to a subjective assessment of similarity clustering of the database VOIs, where the objective assessment of similarity clustering occurs in a feature space and where the optimal set of features is specific to the medical image;

an output module configured to provide the selected set as output; and wherein said selection selects an optimal similarity criterion for use in the fetching of examples.

2. The device of claim 1, wherein said selection selects an inter-point distance metric said optimal similarity criterion comprises, said metric being utilized in the objective-assessment-based clustering in said feature space defined by said selected features.

3. The device of claim 1, wherein the features in said set define said feature space.

4. The device of claim 1, wherein said selection comprises iteratively choosing a set of VOI features to arrive at said optimal set.

5. The device of claim 4, wherein a genetic algorithm performs the iterative choosing.

6. The device of claim 4, wherein a given iteration chooses a respective set which defines a feature space for that iteration.

7. The device of claim 1, wherein the subjective assessing comprises assigning, to said respective clusters, the database VOIs based on perception in pair-wise comparisons of said database modules.

8. The device of claim 1, wherein included among said features is a feature of an image of a VOI of said VOIs.

9. The device of claim 8, wherein included among said features is clinical data relating to a VOI of said VOIs.

10. An example-based computer aided diagnosis system comprising the device of claim 1, said system further comprising:
   a database configured to contain volumes-of-interest (VOIs);
   communicatively connected to said output module, a fetching module configured to evaluate, based on the selected set, a volume-of-interest (VOI) to be diagnosed and for performing, based on an outcome of said evaluating, configured to fetch said examples from said database containing VOIs; and
   a display configured to display the fetched examples.

11. The example-based computer aided diagnosis system of claim 10, further comprising a user control, and a processor configured to cause display, on said display, the fetched examples and, for a displayed one of said fetched examples chosen by means of said user control, at least one of prognosis, therapy information, follow up information, current status, and clinical information retrieved from an electronic medical record (EMR).

12. A computer software product for example-based computer-aided diagnosis comprising a computer readable medium embodying a computer program comprising instructions executable by a processor to perform a plurality of acts, said plurality comprising the acts of:
   selecting an optimal set of volume-of-interest (VOI) features by which to fetch examples such that objective assessment of similarity, based on the selected features, clusters, in a feature space, VOIs in a database so as to conform to clustering of the database VOIs into respective clusters by subjectively assessing similarity;
   fetching examples by using the optimal set of VOI features; and
   causing display of the fetched examples along with at least one of prognosis, therapy information, follow up information, current status, and clinical information retrieved from an electronic medical record (EMR).

13. The product of claim 12, where the at least one of prognosis, therapy information, follow up information, current status, and clinical information retrieved from an electronic medical record (EMR) is selected for display by a user input to a user control.

14. The product of claim 13, comprising:
   where selecting the optimal set is performed by a generic algorithm that iteratively chooses a set of VOI features to arrive at the optimal set, where the optimal set is specific to an item to be diagnosed, and where the item to be diagnosed is displayed along with the fetched examples and the at least one of prognosis, therapy information, follow up information, current status, and clinical information retrieved from an electronic medical record (EMR).

15. A computer-implemented method for optimizing example-based computer-aided diagnosis, comprising:
   clustering volumes-of-interest (VOIs) in a database into respective clusters according to subjective assessment of similarity; and
   selecting an optimal set of volume-of-interest (VOI) features by which to fetch examples such that objective assessment of similarity, based on the selected features, clusters, in a feature space, the database VOIs so as to conform to said clustering, where selecting is performed by a generic algorithm that iteratively chooses a set of VOI features to arrive at said optimal set.

16. The method of claim 15, further comprising utilizing, in the fetching of examples, an optimal similarity criterion said selecting selects.

17. The method of claim 16, wherein said selecting selects an inter-point distance metric said optimal similarity criterion comprises, said metric being utilized in the objective-assessment-based clustering in said feature space defined by said selected features.

18. The method of claim 15, wherein the features in said set define said feature space.

19. The method of claim 15, wherein a given iteration chooses a respective set which defines a feature space for that iteration.

20. The method of claim 15, wherein performing the subjective assessment comprises assigning, to said respective clusters, the database VOIs based on perception in pair-wise comparisons of said database modules.

21. The method of claim 15, wherein included among said features is a feature of an image of a VOI of said VOIs.

22. The method of claim 21, wherein included among said features is clinical data relating to a VOI of said VOIs.

* * * * *